(12) United States Patent
Bacon

(10) Patent No.: US 7,047,964 B2
(45) Date of Patent: May 23, 2006

(54) DISPENSER FOR MEDICAMENT

(75) Inventor: Raymond John Bacon, Hampshire (GB)

(73) Assignee: Clinical Designs Ltd., Emsworth (GB)

( * ) Notice: Subject to any disclaimer, the term of this patent is extended or adjusted under 35 U.S.C. 154(b) by 0 days.

(21) Appl. No.: 10/470,234

(22) PCT Filed: Jan. 24, 2002

(86) PCT No.: PCT/GB02/00285

§ 371 (c)(1),
(2), (4) Date: Nov. 3, 2003

(87) PCT Pub. No.: WO02/058771

PCT Pub. Date: Aug. 1, 2002

(65) Prior Publication Data

US 2004/0069301 A1 Apr. 15, 2004

(30) Foreign Application Priority Data

Jan. 25, 2001 (GB) ................................. 0101945.4
Feb. 16, 2001 (GB) ................................. 0103856.1

(51) Int. Cl.
*A61M 11/00* (2006.01)
*A62B 7/00* (2006.01)
(52) U.S. Cl. .............................. 128/200.23; 128/205.23
(58) Field of Classification Search ...............
128/200.14–200.24, 203.12, 203.23, 202.21,
128/205.23, 203.15; 239/102.1, 102.2
See application file for complete search history.

(56) References Cited

U.S. PATENT DOCUMENTS

| 4,664,107 | A |   | 5/1987  | Wass |                  |
|-----------|---|---|---------|------|------------------|
| 4,984,158 | A | * | 1/1991  | Hillsman | ............... 128/200.14 |
| 5,347,998 | A | * | 9/1994  | Hodson et al. | ........ 128/200.23 |
| 5,415,161 | A |   | 5/1995  | Ryder |                 |
| 5,544,647 | A |   | 8/1996  | Jewett et al. |         |
| 5,794,612 | A |   | 8/1998  | Wachter et al. |        |
| 5,809,997 | A | * | 9/1998  | Wolf | ..................... 128/200.23 |
| 5,839,429 | A |   | 11/1998 | Marnfeldt et al. |     |
| 6,148,815 | A | * | 11/2000 | Wolf | ..................... 128/205.23 |
| 6,152,130 | A |   | 11/2000 | Abrams et al. |        |
| 6,202,642 | B1 | * | 3/2001 | McKinnon et al. | .... 128/200.23 |
| 6,357,442 | B1 | * | 3/2002 | Casper et al. | .......... 128/200.23 |

(Continued)

FOREIGN PATENT DOCUMENTS

WO    PCT/GB98/00770    3/1998

(Continued)

*Primary Examiner*—Teena Mitchell
(74) *Attorney, Agent, or Firm*—Alfred A. Fressola; Ware, Fressola, Van Der Sluys & Adolphson, LLP

(57) ABSTRACT

A dispenser 1 has a source of medicament 2 with a can 3 and a metered dose valve 4. The outlet stem 5 of the valve is fitted to a junction block 6 in a body 7 of the dispenser to which a breath actuated dose release mechanism 8 is connected for release of the medicament through a nozzle 9. The can has an acoustic transducer 11 attached to its side wall 12, in intimate acoustic contact. An electronic package 14, comprising a detection circuit and a driver for a LCD display 15 are also mounted on the can wall, the transducer being connected to the circuit. The detection circuit is arranged to decrement a count shown on the LCD by one for every detection of noise of dispensing/metering of a dose from the can. The detection circuit is programmed to compare the spectrum of the noise with a known dose-dispensing spectrum and to decrement the counter according to the comparison.

22 Claims, 5 Drawing Sheets

U.S. PATENT DOCUMENTS

| | | | |
|---|---|---|---|
| 6,422,234 B1 * | 7/2002 | Bacon | 128/200.14 |
| 6,435,372 B1 * | 8/2002 | Blacker et al. | 222/23 |
| 6,460,537 B1 * | 10/2002 | Bryant et al. | 128/200.23 |
| 6,601,582 B1 * | 8/2003 | Rand et al. | 128/200.23 |
| 6,672,304 B1 * | 1/2004 | Casper et al. | 128/200.23 |
| 6,752,145 B1 * | 6/2004 | Bonney et al. | 128/200.23 |
| 2002/0000225 A1 * | 1/2002 | Schuler et al. | 128/200.14 |
| 2003/0183226 A1 * | 10/2003 | Brand et al. | 128/200.23 |

FOREIGN PATENT DOCUMENTS

| WO | WO 99/64095 | 12/1999 |
|---|---|---|

* cited by examiner

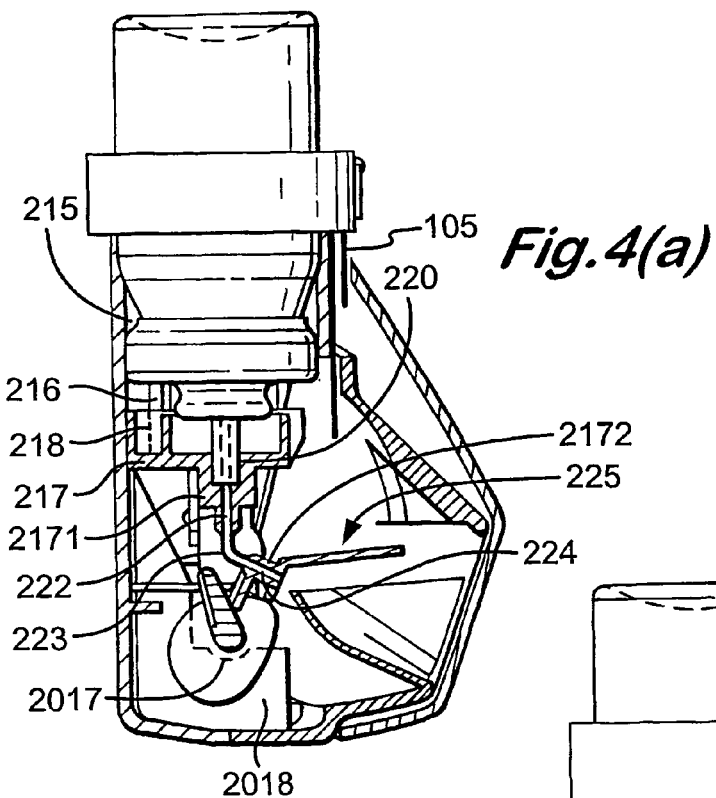
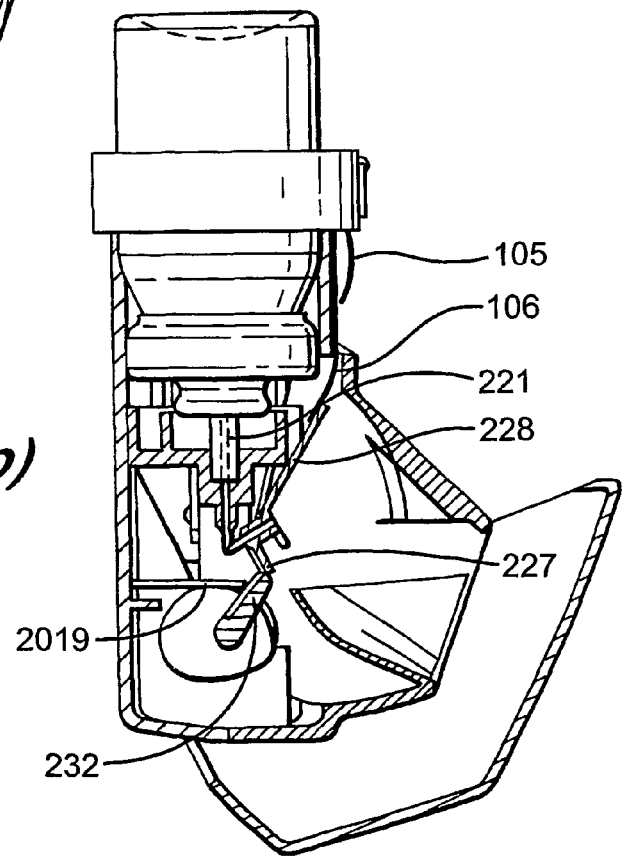

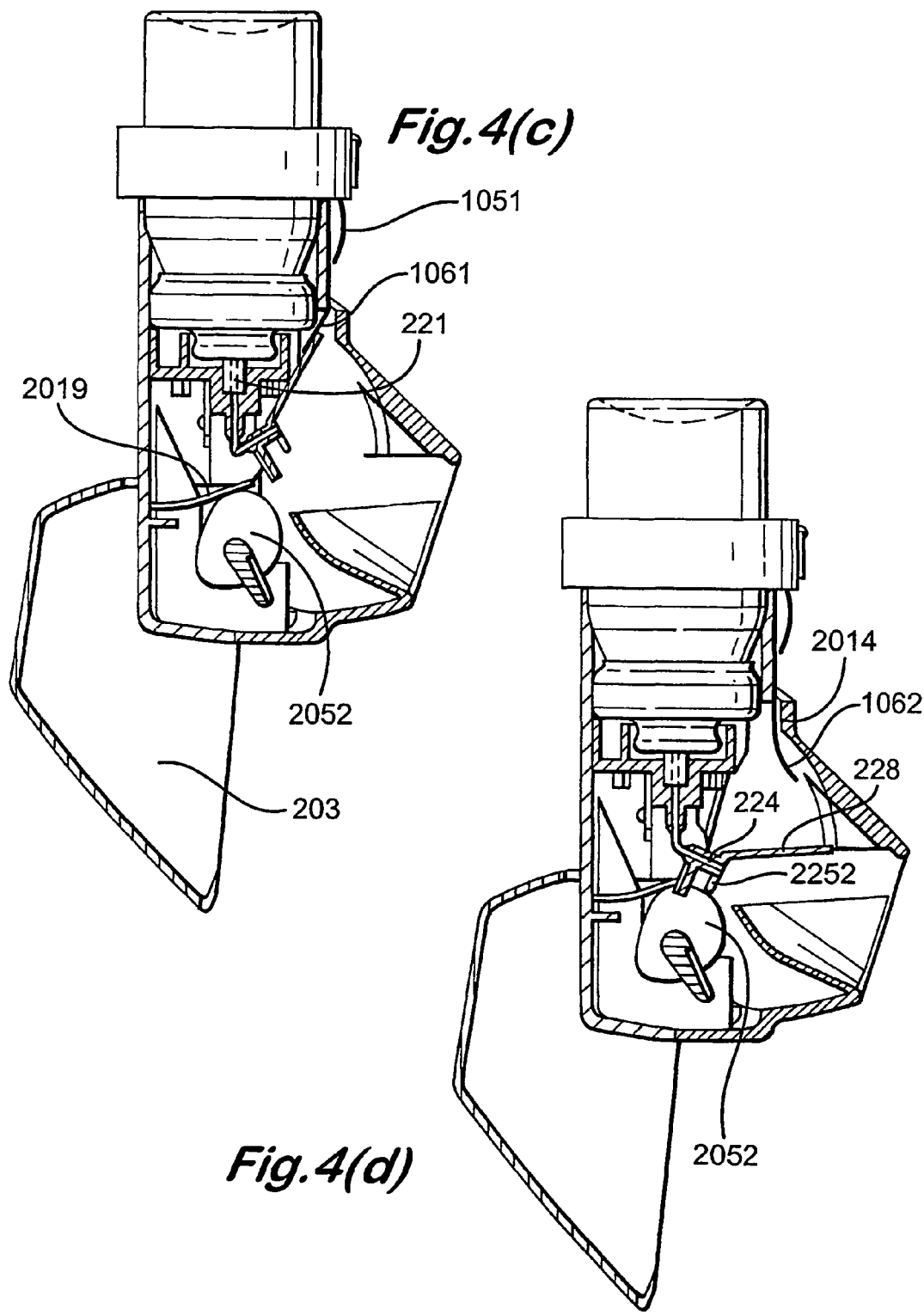

DISPENSER FOR MEDICAMENT

CROSS REFERENCE TO RELATED APPLICATIONS

This application is for entry into the U.S. national phase under §371 for International Application No. PCT/GB02/00285 having an international filing date of Jan. 24, 2002, and from which priority is claimed under all applicable sections of Title 35 of the United States Code including, but not limited to, Sections 120, 363 and 365(c), and which in turn claims priority under 35 USC §119 to Great Britain Patent Application Nos. 0103856.1 and 0101945.4 filed on Feb. 16, 2001 and Jan. 25, 2001, respectively.

TECHNICAL FIELD

The present invention relates to a dispenser for a medicament or the like to be inhaled as successive doses having a counter for such doses and to a counter therefor.

BACKGROUND OF THE INVENTION

By way of illustration, in my prior International Patent Application, PCT/GB98/00770, at least as amended on entry into the European Regional Phase, there is described and claimed:

A dispenser for a gaseous, gas borne or droplet substance, the dispenser including:
  a body having a mouthpiece with an inhalation/insufflation orifice at its end;
  a junction in the body for a source of gas or evaporable liquid comprising or containing the said substance (the source being carried by the body); and
  a breath actuable valve, for controlling the release of said gas or liquid, comprising:
    a valve inlet connected to the junction;
    a valve outlet;
    a flexible tube extending from the junction, between the inlet and the outlet, for receiving the said gas or liquid, the tube having a portion which is movable between a closed position in which the tube is kinked for closure of the valve and an open position in which the tube is un-kinked for opening of the valve; and
    a movable member, for moving the movable portion of the tube to control its kinking, and being movably mounted in the body for movement by the act of inhalation from a rest position towards the orifice—or at least in the direction of air flow through the dispenser;
  the tube being kinked to an obturating extent when the movable member is in a rest position and un-kinked when the movable member is moved on inhalation for release of the gas or liquid.

The source of such a dispenser will typically be a pressurised can, having a valve for metering the dose of substance to be dispensed on each inhalation; although it is conceivable that this or a similar dispenser will dispense a dose which is not metered by the source, but rather is metered by the dispenser by filling of the duct between the source and the dispenser's valve on release of substance from the source.

There has been increasing interest in counting the number of doses dispensed from the source, for instance to alert the user to the number of doses which have been dispensed or more usually of the number of doses of known composition or strength which can still be dispensed.

SUMMARY OF THE INVENTION

The object of the present invention is to provide an improved counter for such a source and dispenser.

According to a first aspect of the invention, there is provided, a dispenser comprising:
  a dispenser body having an inhalation passage leading to a mouthpiece;
  a pressurised source of the medicament arranged at an up-stream end of the inhalation passage;
  a junction in the body for receiving a stem of the pressurised source and directing the pressurised medicament for inhalation;
  means for controlling release of doses from the pressurised source;
  a transducer for detecting gaseous flow within the dispenser associated with release of a dose for inhalation; and
  a counter arranged to be incremented or decremented in accordance with each flow detection by the transducer.

In one embodiment, the source is a metered dose can and the junction includes a simple nozzle for directing the released dose towards the mouthpiece, the dose being released on depression of the can in the body. The transducer is an acoustic transducer arranged to detect noise of gas flow from the can on release of a dose.

Equally it is envisaged that an acoustic transducer detecting gas flow from the can could be provided in a breath actuated dispenser for detecting the preliminary release of the dose from the can prior to breath actuated release.

Conveniently the counter is adapted to recognise the spectrum of a particular gas flow in use of the dispenser. The acoustic transducer can be positioned in acoustic contact with the can, preferably at its side wall, for detecting gas flow to or from a metering chamber in the can. Alternatively, the acoustic transducer can be positioned in acoustic contact with the body of the dispenser for detecting gas flow to or from an intermediate chamber in dispenser.

In another embodiment, the source is a metered dose can, the junction provides connection to a breath actuated dose release mechanism. The transducer is a detector arranged to detect gas flow on inhalation causing the mechanism to release the dose following preliminary release of the dose from the can.

In accordance with a particular feature of the invention, the counter is associated with an indicator, typically audio or visual, for indicating a period of time from dose release during which the user should continue to inhale for drawing the medicament into his lungs or at least hold his breath with the medicament in his lungs to allow it to settle onto the lung lining.

In accordance with another feature, the counter is removably mounted on the dispenser, whereby it can be fitted to another dispenser after the can of a first dispenser has released its prescribed number of doses.

Again, the detector may be arranged to change the state of the counter from quiescent to active on detection of a first event and increment/decrement the counter on detection of a second event. The detector can comprise a single transducer for such two stage action or two transducers can be provided—one for each stage.

According to another aspect of the invention there is provided a counter and transducer for a dispenser according to the first aspect of the invention, the counter and transducer comprising:

a transducer for detecting gaseous flow within the dispenser associated with release of a dose for inhalation; and a counter arranged to be incremented or decremented in accordance with each flow detection by the transducer.

The counter can be arranged merely to count. However, it is envisaged that other functions can also be performed, particularly initiation of a timer to time a delay between inhalation and breath release, to provide time for drug deposition in the lungs.

BRIEF DESCRIPTION OF THE DRAWINGS

To help understanding of the invention, a specific embodiment thereof will now be described by way of example and with reference to the accompanying drawings, in which:

FIG. 4(a) to FIG. 4(d) are cross-sectional views of the second dispenser respectively in closed, half-cock, cocked and open states.

DETAILED DESCRIPTION

Figure 1:
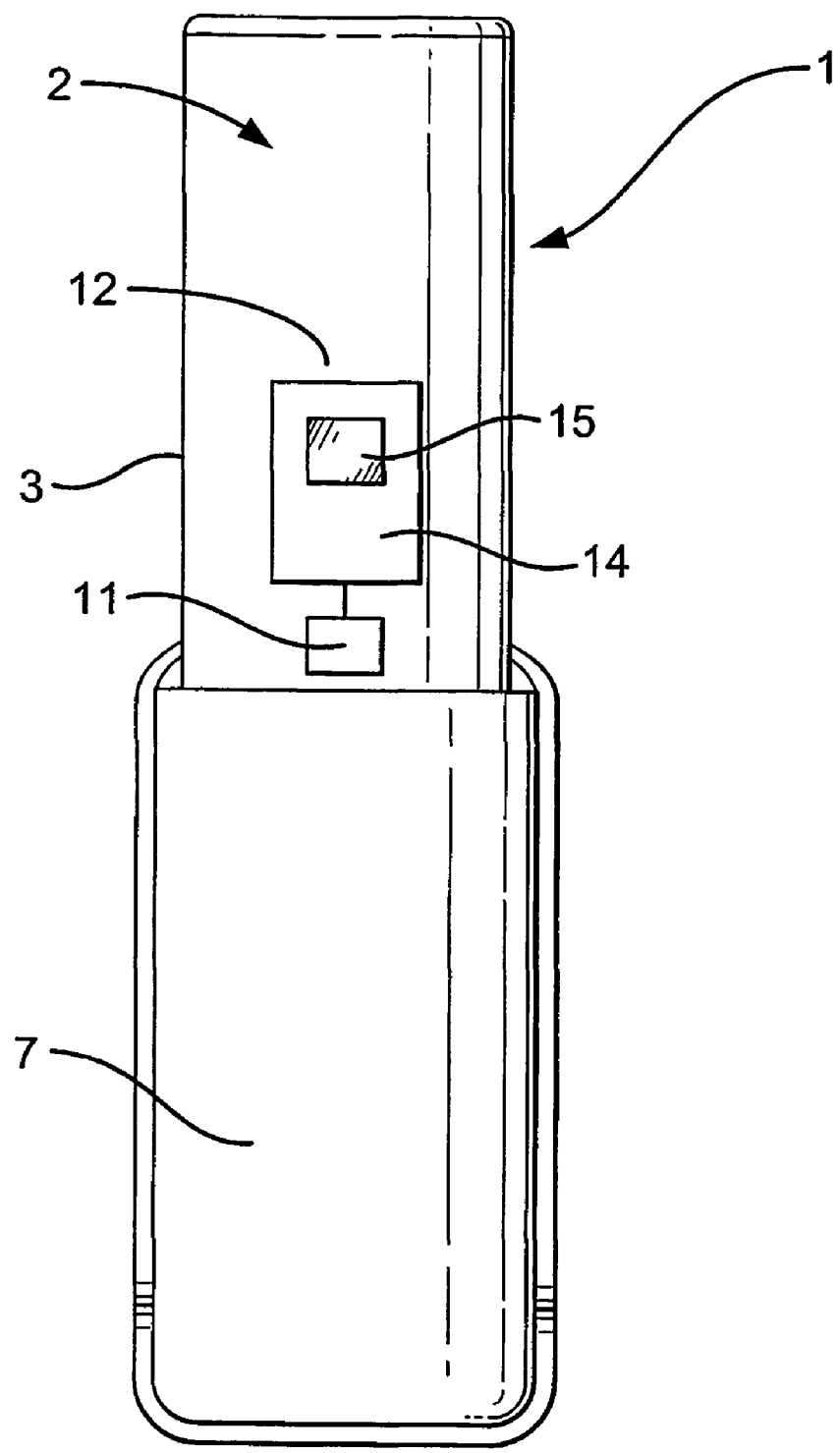
FIG. 1 is a partially cut-away side view of a dispenser having a counter of the invention.
Figure 2:
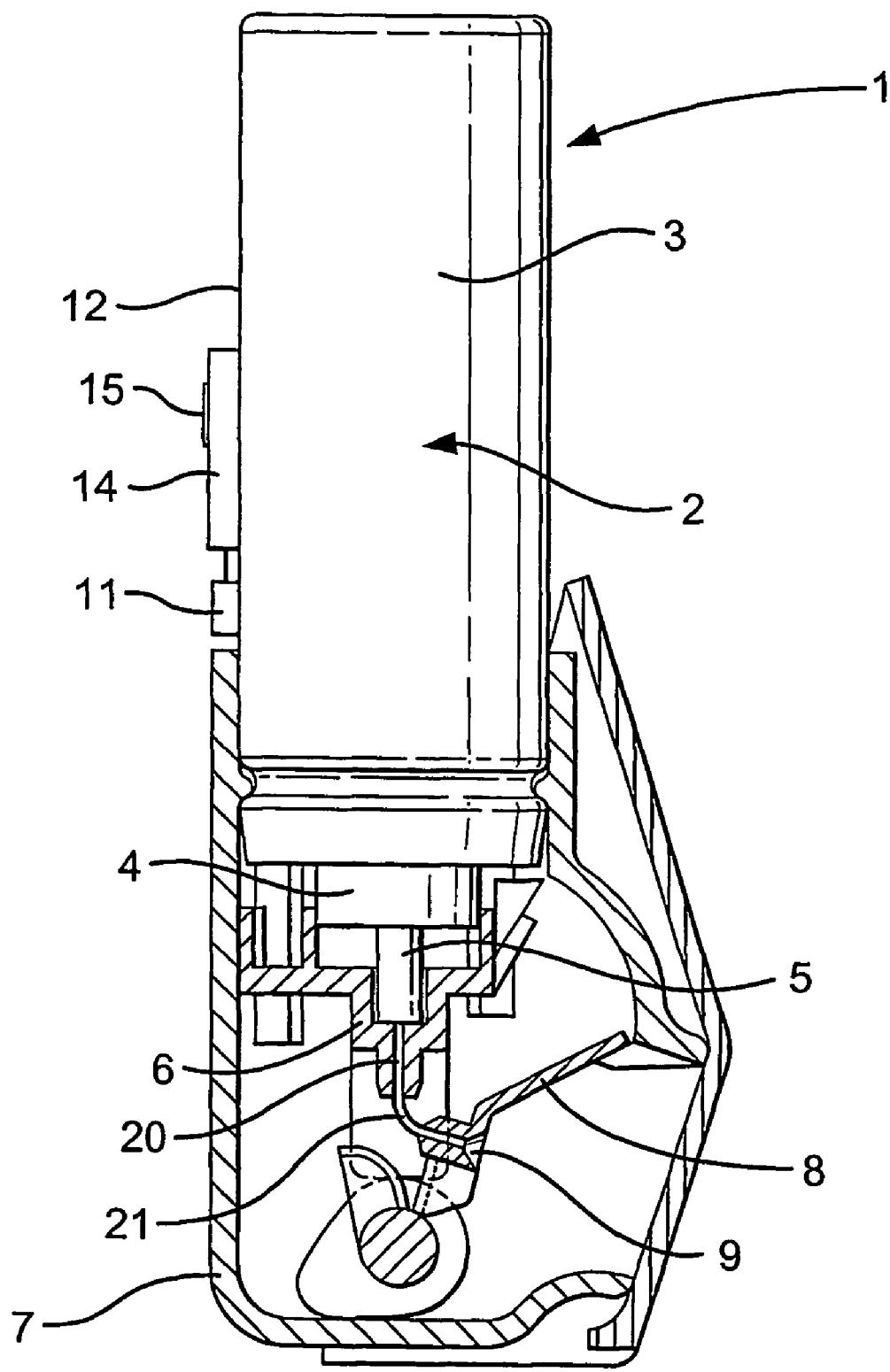
FIG. 2 is an end view of the dispenser.
Figure 3A:
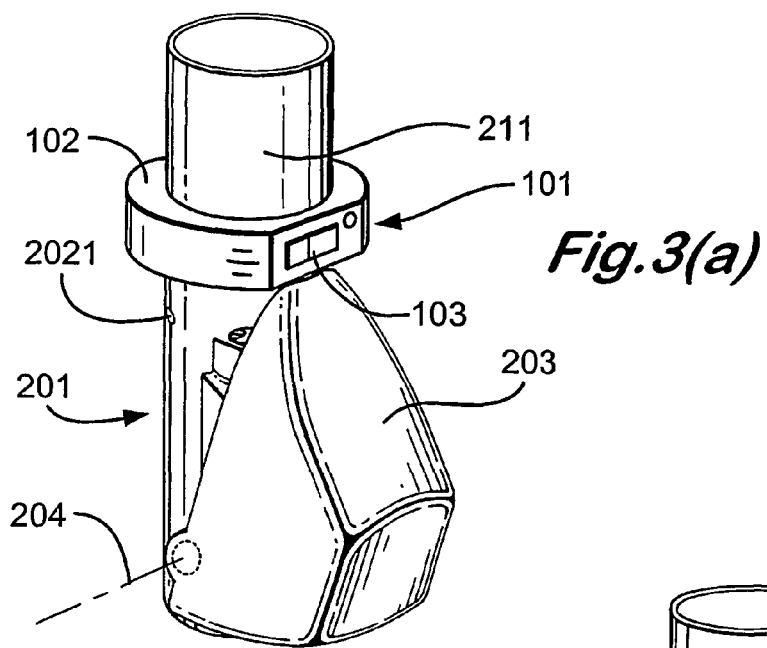
FIG. 3(a) and FIG. 3(b) are perspective views of a second dispenser according to the invention with its cover respectively closed and open.
Figure 3B:
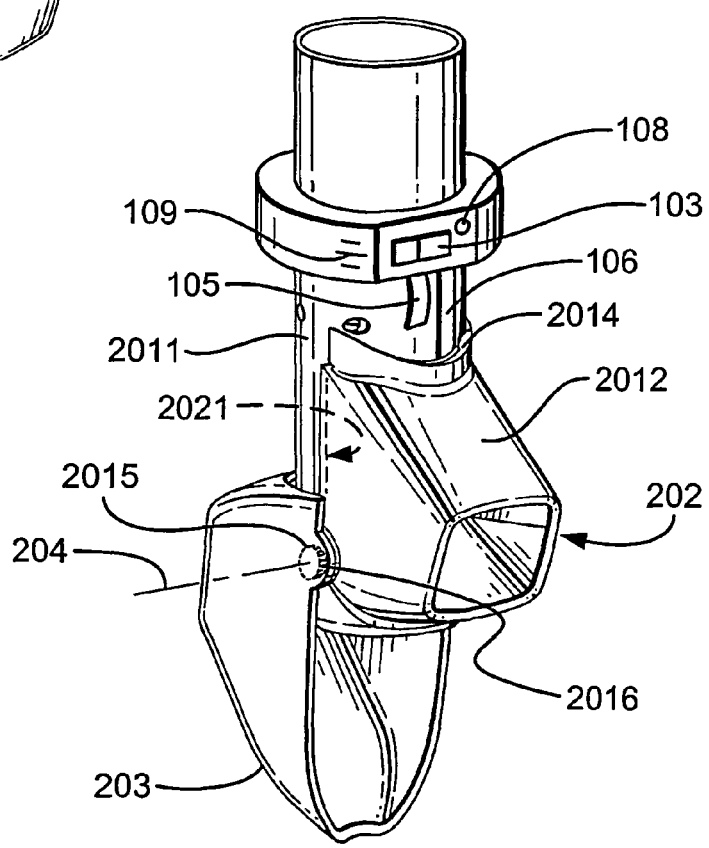

Referring to FIGS. 1 & 2, the dispenser 1 has a source of medicament 2 with a can 3 and a metered dose valve 4. The outlet stem 5 of the valve is fitted to a junction block 6 in a body 7 of the dispenser to which a breath actuated dose release mechanism 8 is connected for release of the medicament through a nozzle 9. Since the mechanism forms no part of the present invention, it will not be described in detail here. It could be configured as in my International Patent Application, PCT/GB01/03313, indeed FIGS. 1 and 2 are based on the second embodiment (FIG. 6 et seq.) of that disclosure.

The can has an acoustic transducer 11 attached to its side wall 12, in intimate acoustic contact. An electronic package 14, comprising a detection circuit and a driver for a LCD display 15 are also mounted on the can wall, the transducer being connected to the circuit. It is believed that the selection of the transducer, detection circuit, driver and display will all be within the capabilities of the man skilled in the art, and as such will not be described here in detail.

The detection circuit is arranged to decrement a count shown on the LCD by one for every detection of noise of dispensing/metering of a dose from the can. In order to avoid a spurious noise being detected as an indication of a dose, the detection circuit is programmed to compare the spectrum of the noise with a known dose dispensing spectrum and to decrement the counter according to the comparison. The counter starts at the manufacturer's recommended number of doses from the can, whereby the user can see how many doses are left to be dispensed and when a new dispenser is about to be needed.

It should be noted that the breath actuated dose release mechanism of the dispenser of FIG. 1 and 2 plays no part in the operation of the dispenser. Rather, the transducer is arranged to detect the noise of a dose being dispensed from the can's internal metering chamber (not shown in detail) to the release mechanism 8, the metering chamber being a standard feature of such a can having a metered dose valve 4 and an outlet stem 5. The arrangement being such that on depression of the stem, a dose held in the metering chamber is released through the stem, and on release of the stem, it is resiliently returned and the metering chamber is replenished. For this the can needs to be inverted as it is in use. This is of particular note in respect of the term depression of the stem, which in this context involves an upwards movement of the stem inwards of the can.

It should also be noted that the transducer—or rather the acoustic recognition firmware in the counter—could be arranged to recognise the noise of the metering chamber refilling. However, it is believed that the noise of it emptying is more distinctive and more readily recognised. It is also conceivable that the firmware should recognise both noises and decrement the counter only on occurrence of every other recognised noise.

Further variants can be envisaged for this embodiment. For instance, the counter can be arranged to increment the displayed count towards a recommended maximum. Also, the transducer, circuitry and display can be arranged elsewhere, such as on the body 7 for detection of flow into an intermediate chamber 20 formed between the can stem 5 and a kink valve 21 in the breath actuated mechanism, whereby the transducer on the body can recognise the noise of the pressurised dose being dispensed through the nozzle.

Referring to FIGS. 3(a) to 4(d), a further metered dose inhaler is thereshown, this is based on the third embodiment of my International Patent Application, PCT/GB01/03313, namely that of FIGS. 13 to 17 thereof. The dispenser thereshown has a body 201 with a mouthpiece 202 and a pivoted mouthpiece cover 203. The mouthpiece is formed as an aperture 2021 in a separate body part 2012 clipped to a main body part 2011. The mouthpiece part is cutaway 2014 with respect to the medicament can 211 fitted to the body, to define an air inlet exposed by the cover when this is open. The cover is pivoted about an axis 204 low in the body at the joint between the two body parts.

The can 211 is held in an opening at the upper end of the main body part 2011 by a pair of location pins in openings in sidewalls of the body part. The pins positively locate the can with respect to the body by engagement in a groove 215 formed in the can for retaining its closure collar. Thus the can and the body 201 are rigidly connected. Also moulded inside the body are internal ribs 216. A junction member 217 is slidably accommodated in the body with the ribs engaging in grooves 218 in its periphery. Centrally, the junction member has a socket 220 for an outlet stem 221 of the can. The socket is continued by a passage 222, which has a thin wall, kinkable portion 223 and a nozzle end 224. This is in a movable outlet member 225 of a valve part 2172 of the junction member. The main part 2171 of the junction member 217 and the valve part 2172 are connected by a living hinge. To both sides of the outlet member are provided flats, which form the base for a breath actuation flap 228 and are connected to the living hinge portions at the outside ends of the flats. A lug 227 depends from the outlet member for engagement with a cam finger 232 extending from between a pair of cam lobes 2052.

To either side of the socket 220 of the junction member, it has two depending fingers arranged to co-operate with the cam lobes at their distal ends. These abut—under the force of the internal spring (not shown) of the can, and with the interposition of two leaves 2019—the cam lobes 2052.

The action of the dispenser is as follows:

On opening of the cover, by swinging about the axis of the cam member, the cam finger 232 acts on the lug 227 to move the outlet member to a position where the flap 228 is lifted and the kinkable portion 223 is closed. In this position, the kink tube is kinked and will not pass a dose about to be released into it.

Further opening of the cover causes the cam lobes 2051, 2052 to lift the junction member and stem 221 towards the can. This releases a dose from the can into the kinked valve, which retains it. The cover stops by abutment with body and the mechanism is cocked and primed for use.

Breathing in through the mouthpiece draws air across the flap, that is round its edges from the air inlet 2014, with a pressure differential developing. Over-centre spring retention of the flap is overcome and it is sprung down to dispense the dose as the outlet nozzle points into the mouthpiece. This, it is free to do since the lug 227 is free of the cam finger 232 at this position.

The mechanism is reset by closure of the cover over the mouthpiece. The junction member drops under the action of the can valve spring and control of the main cam lobes. The cam finger 232 and the flap lug 227 engage on their rear faces, that is the faces opposite from the those which cause lifting of the flap on opening of the cover. Such engagement is unwanted and the faces are provided with complementary wedge shapes—as shown in FIG. 12—whereby the lobe and lug deflect side ways and pass each other. This deflection causes a drag on the lug and keeps the flap in its open position. To ensure that the lobe and lug re-engage for next use, each being thin for deflection, their front faces are provided with complementary V edge.

The action of closing the cover causes the cam fingers (not shown) to engage the flap fingers—should the flap be pivoted towards the can—and pivot the flap to its position in which the nozzle 224 is directed towards the (closed) mouthpiece and the kink tube is unkinked.

A counter 101 is removably mounted on the can 211. It comprises a ring 102 sized to grip the can, yet removable in case of need to refit it to another can. It has an LCD display 103, associated with a counting and timing circuit mounted in the ring. The ring carries two transducing elements. The first is an arched piece of piezoelectric film 105 abutted by the edge of the cover and held flat when the cover is closed. The second is a second piezoelectric film 106 extending through the air inlet 2014, to be abutted by the breath actuation flap 228 when the flap is set to the cocked position in FIG. 4(*c*). This abutment flexes the film from a flat state to which it has a tendency to return.

On opening of the cover, the first film 105 is free to resume its arched state 1051 and in doing so sends a "wake-up" signal to the counter. The flap 228 is set to its cocked state, deflecting the second film 106 to a curved state 1061. This causes it to send a signal to the counter. This is ignored or can be used as an additional wake-up signal or indeed in the possible absence of the film 105, this signal can be the wake-up signal for the counter. On inhalation, two effects combine to flex the second film 106. Firstly the deflection imposed by the flap is removed. Second inhalation air flexes the film to an oppositely curved state 1062. This flexure causes it to generate a "count" signal causes the counter to decrement by one the count of doses shown on the LCD display 103.

Further, the count signal causes the counter to illuminate an LED 108, indicating to the user to keep inhaling or at least to not exhale. The LED can be illuminated with a red colour. At the end of an inhalation period, say two seconds, sufficient for the medicament to reach the user's lungs and begin to settle out of suspension, the LED is caused to change colour to green, indicating to the user that exhalation is now allowed. The LED can be supplemented or replaced by a two tone buzzer 109 or by flashing or other indication from the LCD display.

After use, the cover is closed, flattening the first film 105. The second film 106 takes up a quiescent flat state. It should be noted that second film detects both cocking of the dispenser, when deflected from the quiescent state to the deflected state 1061 imposed by the breath actuation flap 1062, and inhalation gas flow when deflected as a vane by this flow to the deflected state 1062.

Should the inhaler not be used, the act of closure releases the flap, and rests the breath actuated mechanism. This releases the dose against the inside of the cover. It is a dose that is lost. The counter counts this since the deflection of the second flap to its quiescent state causes a signal to be passed to the counter. The latter decrements its displayed count.

In a non-illustrated variant, the piezo-electric strip 106 is arranged not to be deflected, but to experience a change in temperature on inhalation and thus decrement the counter.

In an other non-illustrated variant, the transducers are proximity detectors arranged to detect movement of the cover and the breath actuated flap.

The invention claimed is:

1. A dispenser for a medicament or the like to be inhaled as successive doses, the dispenser comprising:
   a dispenser body having an inhalation passage leading to a mouthpiece;
   a pressurised source of the medicament arranged at an up-stream end of the inhalation passage;
   a junction in the body for receiving a stem of the pressurised source and directing the pressurised medicament for inhalation;
   means for controlling release of doses from the pressurised source;
   a transducer for detecting gaseous flow within the dispenser associated with release of a dose for inhalation; wherein:
      the transducer is an acoustic transducer arranged to detect noise of gas flow within or from the pressurized source of the medicament on release of a dose; and
   a counter arranged to be incremented or decremented in accordance with each flow detection by the transducer, wherein:
      the counter including an associated detection circuit that is adapted to recognise the spectrum of a particular gas flow in use of the dispenser and to increment/decrement the counter in response to such recognition.

2. A dispenser as claimed in claim 1, wherein:
   the source is a metered dose can having a metering chamber;
   the dose release controlling means is a valve in the can arranged to release a dose from the metering chamber on depression of the stem towards the can; and
   the junction includes a connection from the can to the means for controlling release of doses from the pressurized source, the dose being released on depression of the can in the body.

3. A dispenser as claimed in claim 2, wherein the counter is adapted to recognise the spectrum of a particular gas flow in use of the dispenser and to increment/decrement the counter in response to such recognition.

4. A dispenser as claimed in claim 2, wherein the acoustic transducer is positioned in acoustic contact with the can, preferably at a side wall of the can, for detecting gas flow to or from a metering chamber in the can.

5. A dispenser as claimed in claim 2, wherein the acoustic transducer is positioned in acoustic contact with the body of the dispenser for detecting gas flow in a gas passage downstream of the can.

6. A dispenser as claimed in claim 1, wherein:
the source is a metered dose can having a metering chamber;
the dose release controlling means is a breath actuated release mechanism downstream of the junction, the dose being released from the mechanism on inhalation; and
the junction includes a connection from the can to the breath actuated release mechanism, the dose being released on depression of the can in the body.

7. A dispenser as claimed in claim 6, wherein the acoustic transducer is positioned in acoustic contact with the can, preferably at its side wall, for detecting gas flow to or from a metering chamber in the can.

8. A dispenser as claimed in claim 6, wherein the acoustic transducer is positioned in acoustic contact with the body of the dispenser for detecting gas flow in a gas passage downstream of the can.

9. A dispenser as claimed in claim 6, wherein the counter has a quiescent state and an active state and wherein the counter is arranged to change from the quiescent state to the active state on detection of a first event and wherein the counter increments/decrements on detection of a second event.

10. A dispenser as claimed in claim 9, comprising a single transducer for detecting such first event and second event.

11. A dispenser as claimed in claim 9, comprising first and second transducers, the first transducer for detecting such first event and the second transducer for detecting such second event.

12. A dispenser as claimed in claim 11, including a mouthpiece cover and wherein the first transducer is adapted and arranged to detect opening of the cover and the second transducer is the gas flow detection transducer.

13. A dispenser as claimed in claim 12, wherein:
the cover is adapted and arranged to release a dose from the source to the breath actuated release mechanism on opening of the cover and to further release the dose from the breath actuated release mechanism upon closure of the cover without breath actuated dose release and
the counter is arranged to increment/decrement in the event of such closure.

14. A dispenser as claimed in claim 1, wherein:
the source is a metered dose can having a metering chamber;
the dose release controlling means is a breath actuated release mechanism downstream of the junction, the dose being released from the mechanism on inhalation;
the junction includes a connection from the can to the breath actuated release mechanism, the dose being released on depression of the can in the body; and
the transducer is arranged to detect inhalation gas flow within the body.

15. A dispenser as claimed in claim 14, wherein:
the breath actuated release mechanism includes a release flap acted on by inhalation flow and
the transducer is arranged to detect movement of the flap.

16. A dispenser as claimed in claim 14, wherein the transducer is a flow transducer arranged to detect flow of inhalation gas past it.

17. A dispenser as claimed in claim 16, wherein the transducer comprises a vane extending into the inhalation passage and adapted to detect a flow induced pressure differential across the vane.

18. A dispenser as claimed in claim 17, wherein the vane is of piezoelectric film material.

19. A dispenser as claimed in claim 14, wherein the transducer is a temperature transducer arranged to detect flow of gas past the transducer as a change in temperature of gas in contact with the transducer.

20. A dispenser as claimed in claim 19, wherein the temperature transducer is of piezoelectric film material.

21. A dispenser as claimed in claim 1, wherein the counter is associated with an indicator, preferably audio or visual, for indicating a period of time from dose release during which the user should continue to inhale or at least hold his breath for drawing the medicament into his lungs.

22. A dispenser as claimed in claim 1, wherein the counter is removably mounted on the dispenser, whereby it can be fitted to another dispenser after the pressurized source of the medicament of a first dispenser has released a prescribed number of doses.

* * * * *